United States Patent [19]

Snell

[11] Patent Number: 5,720,771
[45] Date of Patent: Feb. 24, 1998

[54] METHOD AND APPARATUS FOR MONITORING PHYSIOLOGICAL DATA FROM AN IMPLANTABLE MEDICAL DEVICE

[75] Inventor: Jeffery D. Snell, Oak Park, Calif.

[73] Assignee: Pacesetter, Inc., Sylmar, Calif.

[21] Appl. No.: 510,366

[22] Filed: Aug. 2, 1995

[51] Int. Cl.$^6$ ........................................ A61B 5/02
[52] U.S. Cl. ...................... 607/60; 607/32; 607/63; 607/62; 128/903; 128/696
[58] Field of Search ................ 128/903, 904, 128/696; 607/60, 30, 32, 18, 62, 63

[56] References Cited

U.S. PATENT DOCUMENTS

| Re. 32,361 | 2/1987 | Duggan | 128/903 |
|---|---|---|---|
| 3,724,455 | 4/1973 | Unger | 128/903 |
| 3,782,367 | 1/1974 | Hochberg et al. | 128/2.06 A |
| 4,098,267 | 7/1978 | Stein et al. | 128/2.06 G |
| 4,150,284 | 4/1979 | Trenkler et al. | 250/199 |
| 4,216,462 | 8/1980 | McGrath et al. | 128/904 |
| 4,596,255 | 6/1986 | Snell et al. | 128/697 |
| 4,675,656 | 6/1987 | Narcisse | 128/903 |
| 4,791,936 | 12/1988 | Snell et al. | 128/697 |
| 4,803,625 | 2/1989 | Fu et al. | 364/413.03 |
| 4,809,697 | 3/1989 | Causey, III et al. | 128/419 PT |
| 4,825,869 | 5/1989 | Sasmor et al. | 128/419 PT |
| 4,854,328 | 8/1989 | Pollack | 128/903 |
| 4,889,131 | 12/1989 | Salem et al. | 128/903 |
| 4,952,928 | 8/1990 | Carroll et al. | 128/903 |
| 4,974,607 | 12/1990 | Miwa | 128/903 |
| 5,012,411 | 4/1991 | Policastro et al. | 364/413.06 |
| 5,036,852 | 8/1991 | Leishman | 128/904 |
| 5,038,800 | 8/1991 | Uba | 128/903 |
| 5,113,869 | 5/1992 | Nappholz et al. | 128/903 |
| 5,319,335 | 6/1994 | Russek | 128/903 |
| 5,335,664 | 8/1994 | Nagashima | 128/903 |
| 5,336,245 | 8/1994 | Adams et al. | 128/904 |
| 5,417,222 | 5/1995 | Dempsy et al. | 128/903 |
| 5,522,396 | 6/1996 | Langer et al. | 128/903 |

*Primary Examiner*—William E. Kamm
*Assistant Examiner*—Kennedy J. Schaetzle

[57] ABSTRACT

A monitoring system is provided that monitors the condition of a patient by analyzing physiological data received from implantable medical devices. The monitoring system has at least one monitoring unit, which preferably is suitable for stand-alone operation, or which may be connected to a central monitoring station. The monitoring unit, which receives the physiological data from the implantable medical devices via telemetry, determines whether a patient's physiological condition warrants attention. If the patient's condition is determined to be abnormal, the monitoring unit generates an audible alarm signal or generates an alarm signal that is transmitted to the central monitoring station.

25 Claims, 4 Drawing Sheets

METHOD AND APPARATUS FOR MONITORING PHYSIOLOGICAL DATA FROM AN IMPLANTABLE MEDICAL DEVICE

BACKGROUND OF THE INVENTION

This invention relates to systems for monitoring the physical condition of patients with implantable medical devices. More particularly, the invention relates to a monitoring system in which telemetered signals are received from an implantable device and corresponding data and alarm signals are provided to a central monitoring station.

It is often desirable to closely monitor the physical condition of patients in a health care facility. In hospitals, the various monitors that are used, such as blood pressure monitors, respiratory monitors, and electrocardiograph (EKG) machines, are capable of triggering alarms if an abnormal condition is detected. For example, if a patient's heartbeat drops below a predefined threshold, an EKG machine will produce an audible alarm that alerts nearby medical personnel.

It is also possible to interconnect physiological monitors to a central monitoring station, which allows the physical condition of many patients to be monitored by a relatively small staff. If a monitor detects an abnormal physiological condition in a patient, the staff at the central monitoring station can be notified immediately. For example, if an EKG machine detects a patient's low heart rate, an alarm signal can be transmitted to the central monitoring station. Alarm signals are sent either in response to a periodically received command from the central monitoring station or asynchronously, depending on the communication protocol used by the monitoring system.

Although conventional physiological monitors are generally reliable, if a patient has a pacemaker or similar cardiac stimulating device, an unsophisticated EKG machine may misidentify pacing pulses as heartbeats. Further, some of the physiological data that reveals the most about a patient's condition is measured internally, using implantable medical devices, such as implantable cardiac stimulating devices, implantable cardiac monitoring devices, and implantable drug pumps. With conventional monitoring systems, internally measured data is unavailable at the central monitoring station.

Implantable cardiac monitoring devices use sensors to detect and record various cardiac characteristics and provide performance and trending information that can be used to establish the condition of the heart. Sensors may be used to measure a patient's intracardiac electrogram, heart motion, internal temperature, respiration rate, stroke volume, or activity for analysis and recording. Further, cardiac monitoring devices can transmit the sensor measurements and recordings to an external receiver using telemetry.

Implantable cardiac stimulating devices, such as pacemakers, cardioverters, and defibrillators, use sensors to detect various cardiac abnormalities and provide corresponding corrective therapies to a patient's heart. Sensors may be used to measure a patient's intracardiac electrogram, heart motion, internal temperature, respiration rate, stroke volume, or activity to determine the appropriate electrical pulses to apply to the patient's heart. Further, cardiac stimulating devices and cardiac monitoring devices can transmit sensor measurements to an external receiver using telemetry.

The external receiver is typically a "programmer", which can be used to program the settings of the cardiac stimulating device, as described in commonly-assigned U.S. Pat. No. 4,809,697. A physician uses the programmer to direct a cardiac stimulating device to transmit the signals measured by sensors in the cardiac stimulating device, so that the programmer can analyze and display this data. For example, the cardiac stimulating device (or cardiac monitoring device) can be directed to transmit the measured intracardiac electrogram to the programmer, where it can be displayed in real time, for the physician's review.

Cardiac stimulating devices and cardiac monitoring devices that measure a patient's intracardiac electrogram can also determine which portions of the intracardiac electrogram signals correspond to certain cardiac events, such as R-waves or P-waves or dangerous heart conditions such as the onset of tachycardia. Event markers, such as the letter "R" to represent a measured R-wave, can be transmitted to a programmer and displayed adjacent to the portion of the intracardiac electrogram signal that corresponds to the event.

Although programmers are used extensively by physicians to examine the physical condition of patients by obtaining internally measured physiological data, programmers have not been used for unattended long-term hospital monitoring. As a result, it has not been possible to use internally measured patient data to generate an alarm or to provide internally measured patient data to a central monitoring station, where it could be used to monitor a patient's physical condition.

SUMMARY OF THE INVENTION

In accordance with the principles of the present invention, a monitoring unit and preferably a system for monitoring a patient's physical condition are provided. In contrast to previously known monitoring units and monitoring systems, the present apparatus allows the data measured by an implantable medical device to be used to generate an alarm and to be transmitted via telemetry to a monitoring unit. If desired, the monitoring unit may be connected to a central monitoring station. In a preferred embodiment, a monitoring unit is provided that receives physiological data from cardiac stimulating devices and cardiac monitoring devices. The monitoring unit analyzes a patient's physiological data and provides an alarm or alerts a central monitoring station if the patient's condition is determined to warrant attention.

A user enters commands for controlling the monitoring unit using an input interface, such as a flat panel display/touch screen or a pen and a digitizing screen for capturing the movements of the pen. The monitoring unit is preferably connected to the central monitoring station via a bus, which may allow the transmission of at least some real-time data from the implantable medical device to the central monitoring station, although the monitoring unit may also operate as a stand-alone device. The central monitoring station hardware can be of a conventional design, containing a microprocessor for executing control code, as well as at least one display and user interface. The central monitoring station also contains suitable bus interface circuitry for transmitting and receiving data over the bus.

The monitoring unit can preferably monitor and measure a plurality of parameters including, for example, heart rate, R-wave to R-wave/P-wave to R-wave, capture thresholds, sensing thresholds, lead impedance, sensor readings, and real-time marker codes. Alarm thresholds may be set corresponding to any combination of these signals. When an alarm condition is determined to exist, the monitoring unit generates an alarm signal, either as a local audible or visual alarm signal, or for transmission to the central monitoring station, to notify the hospital staff. If desired, medical personnel can intervene immediately upon receipt of an alarm signal. Staff members at the central monitoring station can also examine the current status of a patient at any time by directing the monitoring unit to provide real-time data from the implantable medical device.

Preferably, the monitoring unit monitors the patient's heart rhythm. If the heart rate is too fast or too slow, the monitoring unit generates the alarm signal.

The monitoring unit can track the operation of the cardiac monitoring device or cardiac stimulating device by interpreting the event marker codes ("markers") that are received from the device. The marker codes allow the monitoring device to determine the "state" of the cardiac monitoring or cardiac stimulating device, from which the condition of the heart and the implanted device can be determined. For example, when the device detects accelerated ventricular contractions in the absence of preceding atrial activity, the existence of premature ventricular contractions of the heart can be deduced. Fluctuations in the lead impedance indicate that a lead may have become dislodged. The "state machine" analysis technique can also be used to generate an alarm signal when the cardiac monitoring or cardiac stimulating device enters a specified mode, such as "automatic mode switching" or a tachycardia termination mode.

The monitoring unit may be implemented using any one of various viable hardware platforms. For example, the monitoring unit may be implemented using a tablet computer and a base station. Alternatively, the monitoring unit may be implemented using a unit that has a flat panel display/touch screen. Control code that is executed by the monitoring unit controls the operation of the monitoring unit, allowing the monitoring unit to monitor the patient's condition and communicate with the central monitoring station. The monitoring unit preferably has a telemetry port, to which a telemetry head is connected. Alternatively, a long-range telemetry head may be incorporated into the monitoring unit. The monitoring unit preferably is connected to the bus via a bus port, which is internally connected to the bus interface.

The operation of the monitoring system is controlled primarily by the physician or a member of the hospital staff who controls the monitoring unit, although the staff member who attends the central monitoring station may direct the monitoring unit to transmit additional physiological data to the central monitoring station, if desired. Typically, the physician selects the limits that trigger the alarm signal.

BRIEF DESCRIPTION OF THE DRAWINGS

The above and other advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Figure 1:
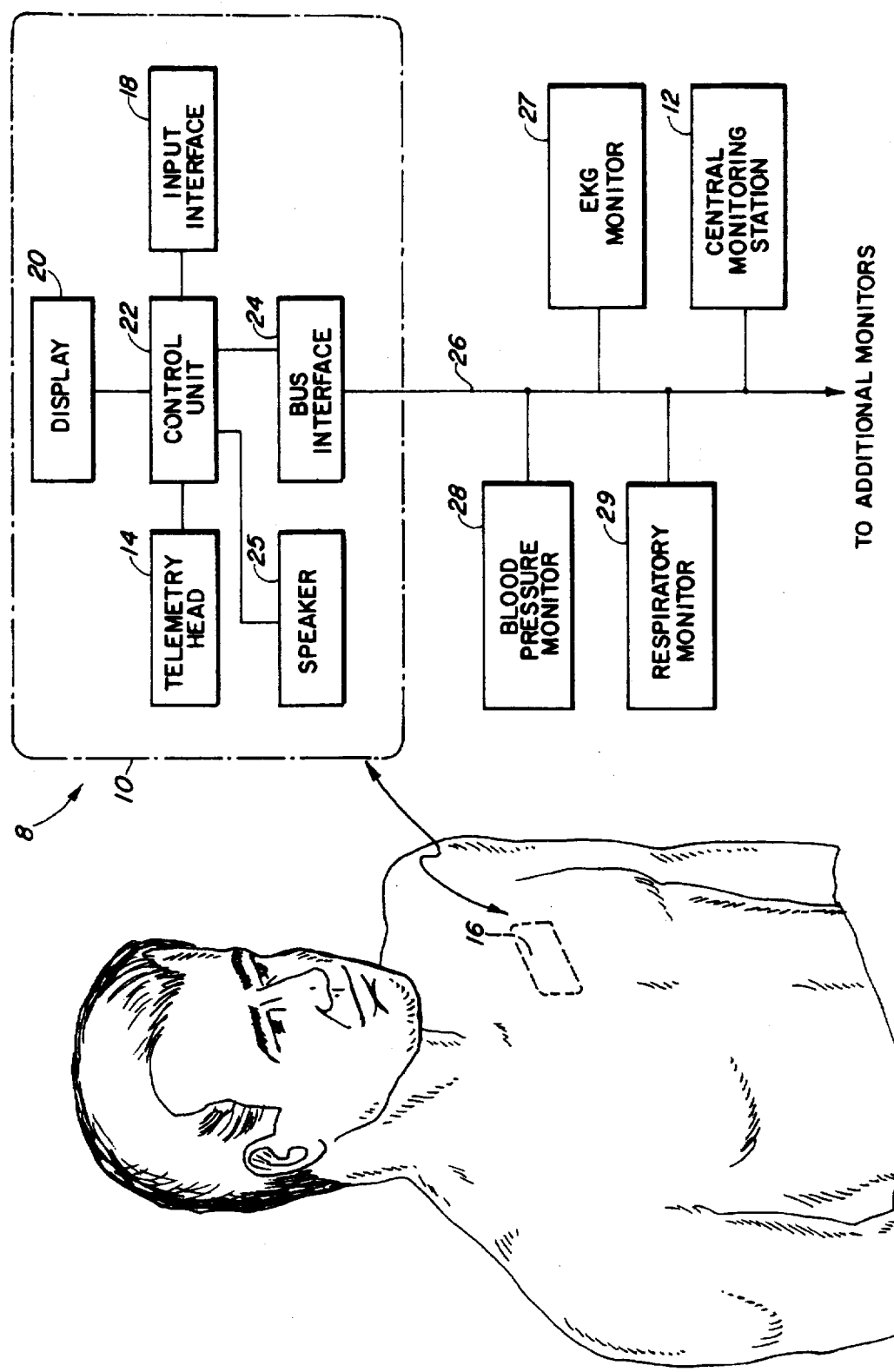
FIG. 1 is a schematic block diagram of a system for monitoring a patient's physical condition in accordance with the present invention.

As shown in FIG. 1, a monitoring system 8 is provided that includes at least one monitoring unit 10 and an optional central monitoring station 12. The monitoring unit 10 includes a standard telemetry head 14 for communication with an implantable medical device 16 via telemetry. A user enters commands for controlling the monitoring unit 10 using an input interface 18, which may be any convenient user interface such as a touch screen, keyboard, light pen, mouse, trackball, or a pen and a digitizing screen for capturing the movements of the pen. Monitoring unit 10 contains a display 20, which can be a cathode ray tube or a liquid crystal display screen. By manipulating the input interface 18, the user can direct a control unit 22 to place physiological data, such as a patient's intracardiac electrogram, on the display 20. In one embodiment, the telemetry head 14, the input interface 18, the display 20, and the control unit 22 can perform the functions of a tablet computer-based programmer of the type described in commonly-assigned, copending U.S. patent application Ser. No. 08/510,367, of Snell, entitled "IMPROVED USER INTERFACE FOR AN IMPLANTABLE MEDICAL DEVICE USING AN INTEGRATED DIGITIZER DISPLAY SCREEN," filed concurrently herewith, which is hereby incorporated by reference herein in its entirety. In a preferred embodiment, a platform is used such as that described in commonly-assigned U.S. Pat. No. 4,809,697, to Causey III et al., which is hereby incorporated by reference herein in its entirety. Although the monitoring unit 10 may be used as a programmer, when the monitoring unit 10 is used to monitor a patient's condition, it is generally left unattended for long periods of time. Because monitoring units 10 may operate unattended for hours, the physiological condition of a number of patients can be simultaneously monitored by a small hospital staff at the central monitoring station 12. The monitoring unit 10 can also be used for stand-alone operation.

The monitoring unit 10 preferably has a bus interface 24, which allows the monitoring unit 10 to communicate with the central monitoring station 12 via a bus 26. The bus interface 24 is not necessary if the monitoring unit 10 is operated as a standalone unit. Any bus that provides a sufficient bandwidth to convey a useful quantity of patient data to the central monitoring station 12 can be used. Preferably, the bandwidth of the bus 26 allows the transmission of at least some real-time data from the implantable medical device 16 to the central monitoring station 12. The addition of the monitoring unit 10 does not preclude the use of conventional monitors, such as an EKG monitor 27, a blood pressure monitor 28, and a respiratory monitor 29, which can still be connected to the bus 26. Further, by using distinct bus addresses, many monitoring units 10 can be used, each connecting a separate implantable medical device 16 to the bus 26.

In operation, physiological data and event markers are transmitted from the implantable medical device 16 and analyzed by the control unit 22 to determine whether a patient's condition warrants generating an audial or visual alarm signal or transmitting an alarm signal to the central monitoring station 12.

If an alarm condition is detected, the monitoring unit 10 generates an alarm signal. The presence of an alarm condition can be indicated visually on the display 20 or audially using a speaker 25, if the monitoring unit 10 is operating as a stand-alone unit. If, however, the monitoring unit 10 is connected to a central monitoring station 12, alarm signals are sent by the monitoring unit 10 to the central monitoring station 12 when an alarm condition is detected. Alarm signals can be sent asynchronously, or alarm signals may be released from the monitoring unit 10 only on receipt of alarm request signals from the central monitoring station 12, depending on the communication protocol used by the monitoring system 8. If the implantable medical device 16 is a cardiac stimulating device, the control unit 22 can calculate the patient's heart rate. If the heart rate is too fast or too slow an alarm signal may be indicated using speaker 25 or display 20, or the control unit 22 can use the bus interface 24 to relay an alarm signal to the central monitoring station 12, thus notifying the hospital staff. Medical personnel can intervene immediately upon receipt of an alarm signal. Alternatively, the staff at the central monitoring station 12 can examine the current status of the patient in more detail by sending commands via the bus 26 that direct the monitoring unit 10 to place additional real-time data from the implantable medical device 16 on the bus 26.

Central monitoring stations for monitoring the physiological condition of patients in a hospital setting are well-known. Preferably, the hardware of the central monitoring station 12 is based on conventional components and contains a microprocessor (not shown) for executing control code, as well as at least one display and user interface (not shown). The central monitoring station 12 also contains suitable bus interface circuitry compatible with the communication protocol used by the monitoring unit 10 for transmitting and receiving data over the bus 26. The capabilities of the monitoring system 8 are dictated to a large degree by the capabilities of the central monitoring station 12, irrespective of the capabilities of the monitoring unit 10. For example, a conventional central monitoring station 12 may be capable of receiving alarm signals from the monitors, such as EKG monitor 27, but may not be capable of handling more complex data, such as real-time physiological data. In a preferred embodiment of the present invention, the monitoring unit 10 is compatible with conventional central monitoring station hardware and software, so that it is not necessary to incur the expense of replacing an existing monitoring system with both a new central monitoring station 12 and new monitoring units 10. Rather, one or more monitoring units 10 can be added to an existing set-up.

The monitoring unit 10 can preferably perform more complex operations when connected to a more sophisticated central monitoring station 12. For example, if the central monitoring station 12 that is used has hardware that allows bidirectional communication with the monitoring unit 10, the central monitoring station 12 may be provided with control software that allows a staff member at the central monitoring station 12 to request that a connected monitoring unit 10 send patient data to the central monitoring station 12 via the bus 26. If the central monitoring station 12 that is in use at a hospital already has the capacity to request that the monitors, such as EKG monitor 27, provide physiological data on demand, the monitoring unit 10 will preferably recognize the format of the data request commands from the central monitoring station 12.

The monitoring unit 10 also may contain a speaker 25, which allows the monitoring unit 10 to produce an audible alarm signal when operating as a stand-alone unit. Alternatively, a visual indication of the alarm signal may be placed on display 20. The bus interface 24 is not necessary if it is only desired to operate the monitoring unit 10 as a stand-alone unit.

Figure 2:
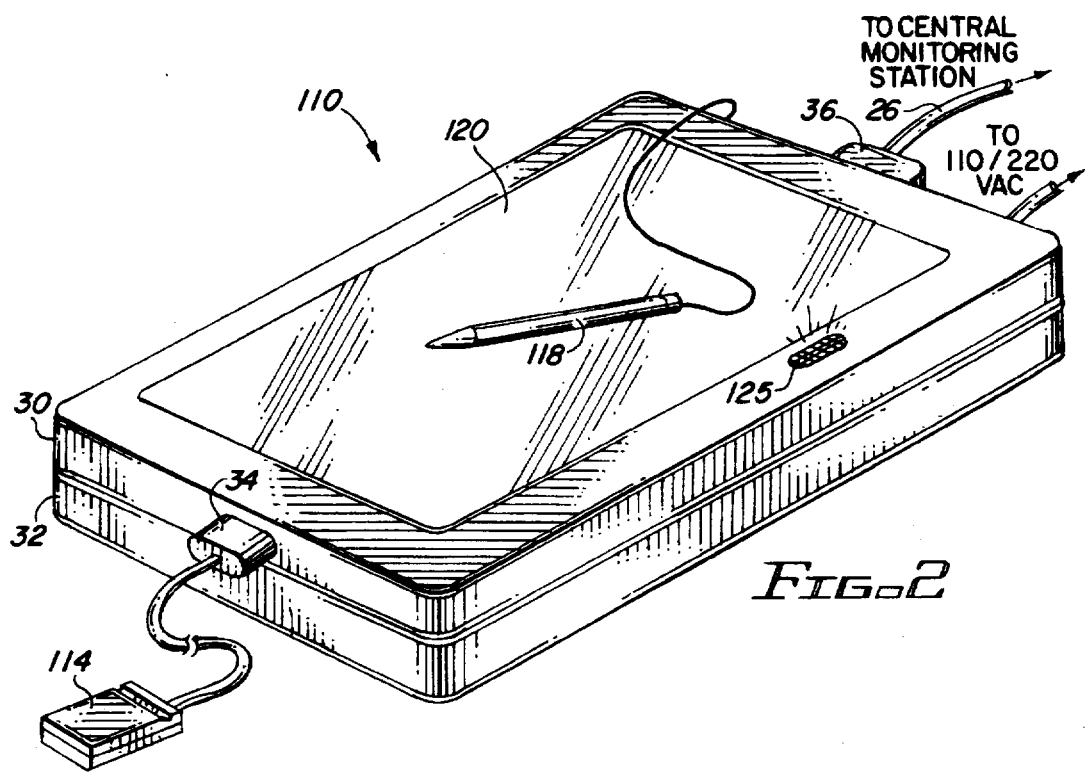
FIG. 2 is a perspective view of a monitoring unit implemented using a tablet computer in accordance with the present invention.

As shown in FIG. 2, the monitoring unit 110 may be implemented using a tablet computer 30 and a base station 32. The tablet computer 30 has an input interface 118, which is a digitizing screen and pen. The tablet computer 30 also has a liquid crystal display 120, a speaker 125, and a standard telemetry head 114. Although the control unit 22 (FIG. 1) can be implemented using any suitable control circuitry, including circuitry other than computer-based circuitry, in a preferred embodiment the control unit 22 is microprocessor-based, so that microprocessor control code can be executed. The control code directs the monitoring unit 110 to monitor the patient's condition and to communicate with the central monitoring station 12 (FIG. 1). The tablet computer 30 contains a battery so that the tablet computer 30 can be removed from the base station 32 when desired, for example, when being used as a programmer, as described in the above-incorporated U.S. patent application Ser. No. 08/510,367, entitled "IMPROVED USER INTERFACE FOR AN IMPLANTABLE MEDICAL DEVICE USING AN INTEGRATED DIGITIZER DISPLAY SCREEN." When used as a monitoring unit 110, the tablet computer 30 is attached to the base station 32, which supplies power to the tablet computer 30.

The tablet computer 30 has a telemetry port 34, to which the telemetry head 114 is connected. The monitoring unit 110 is connected to bus 26 via bus connector 36, which is preferably part of base station 32. The bus interface 24 (FIG. 1) can be attached to the tablet computer 30 either externally, as an optional component, or may be provided internally as either a standard component or an optional card. Preferably, the bus interface 24 (FIG. 1) is an integral component of the base station 32 that is connected to the bus 26 with the bus connector 36. Although not shown, base station 32 may also contain interfaces for connecting various peripheral components and may contain an integral printer. When transmitting data to the central monitoring station 12 (FIG. 1), the bus interface 24 (FIG. 1) receives data from the control unit 22 (FIG. 1) and provides data as buffered data output signals on the bus 26. The bus interface 24 (FIG. 1) may also receive signals from the central monitoring station 12 (FIG. 1) via the bus 26.

Figure 3:
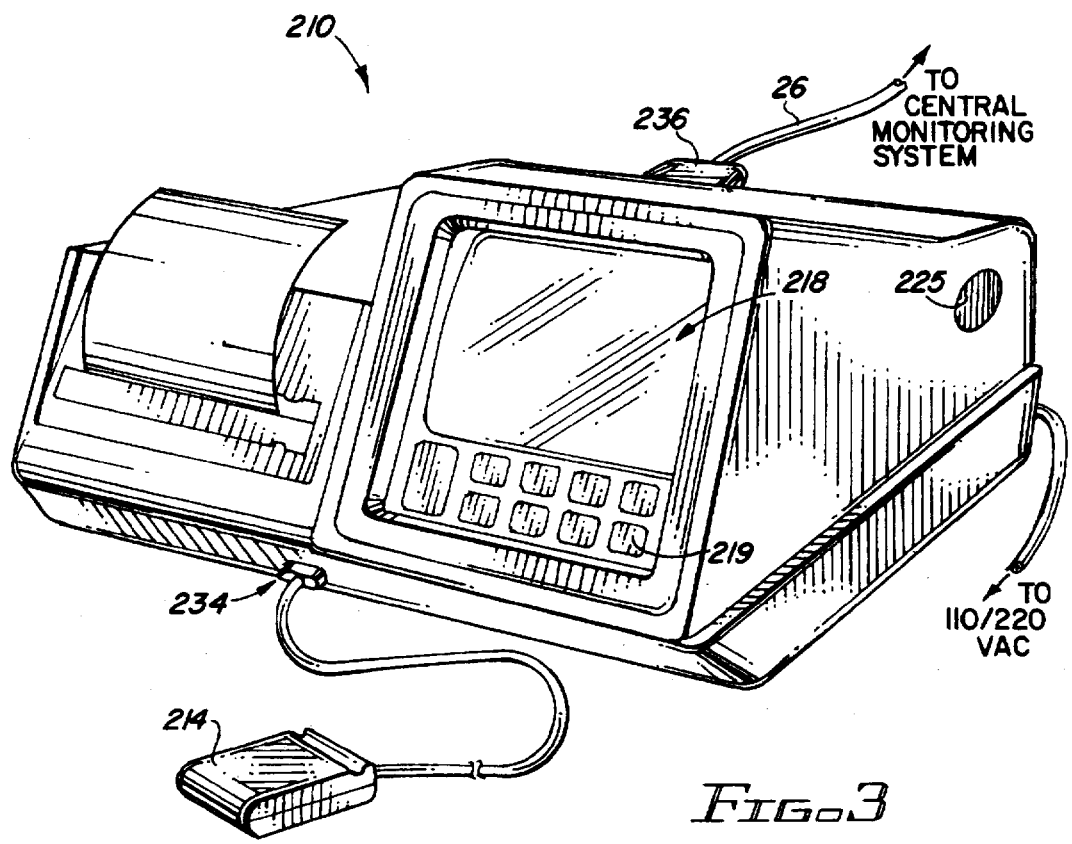
FIG. 3 is a perspective view of a monitoring unit implemented using a flat panel display/touch screen in accordance with the present invention.
Figure 6:
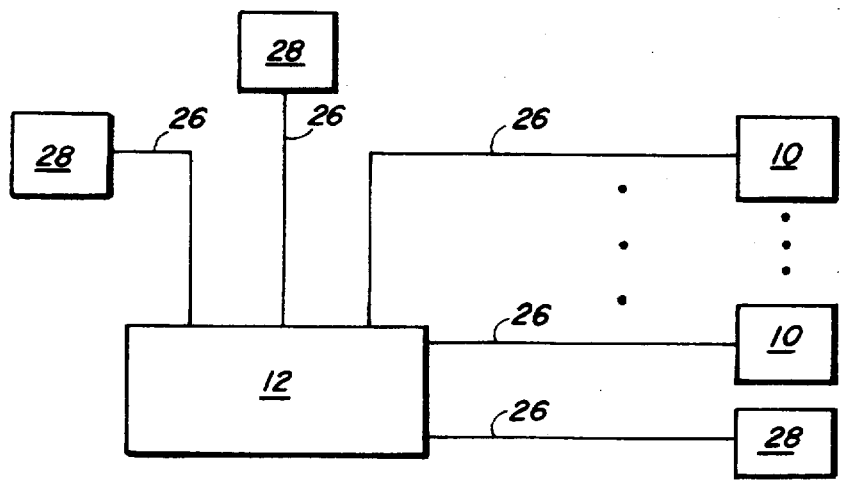
FIG. 6 is a schematic block diagram of the monitoring system in a star configuration in accordance with the present invention.

As shown in FIG. 3, in a preferred embodiment, the monitoring unit 210 uses a flat panel display/touch screen 218 and buttons 219 as the user interface 18 and display 20 (FIG. 1). The monitoring unit 210 has speaker 225 to provide an audible alarm when the monitoring unit is operated in the stand-alone mode. The monitoring unit 210 has a telemetry head 214, which is connected to the monitoring unit 210 via a telemetry port 234. A bus connector 236, to which the bus 26 is connected, is mounted to the rear of the monitoring unit 210. The construction and operation of the monitoring unit 210 is similar to that of monitoring unit 110, except that the user interfaces with the monitoring unit 210 using the flat panel display/touch screen 218 and buttons 219, instead of the pen and digitizing screen 118 and the liquid crystal display 120.

The operation of the monitoring system 8 (FIG. 1) is controlled primarily by a physician or a member of the medical staff who controls the monitoring unit 10, although a staff member at the central monitoring station 12 may occasionally direct the monitoring unit 10 to transmit additional physiological data to the central monitoring station 12.

Figure 4:
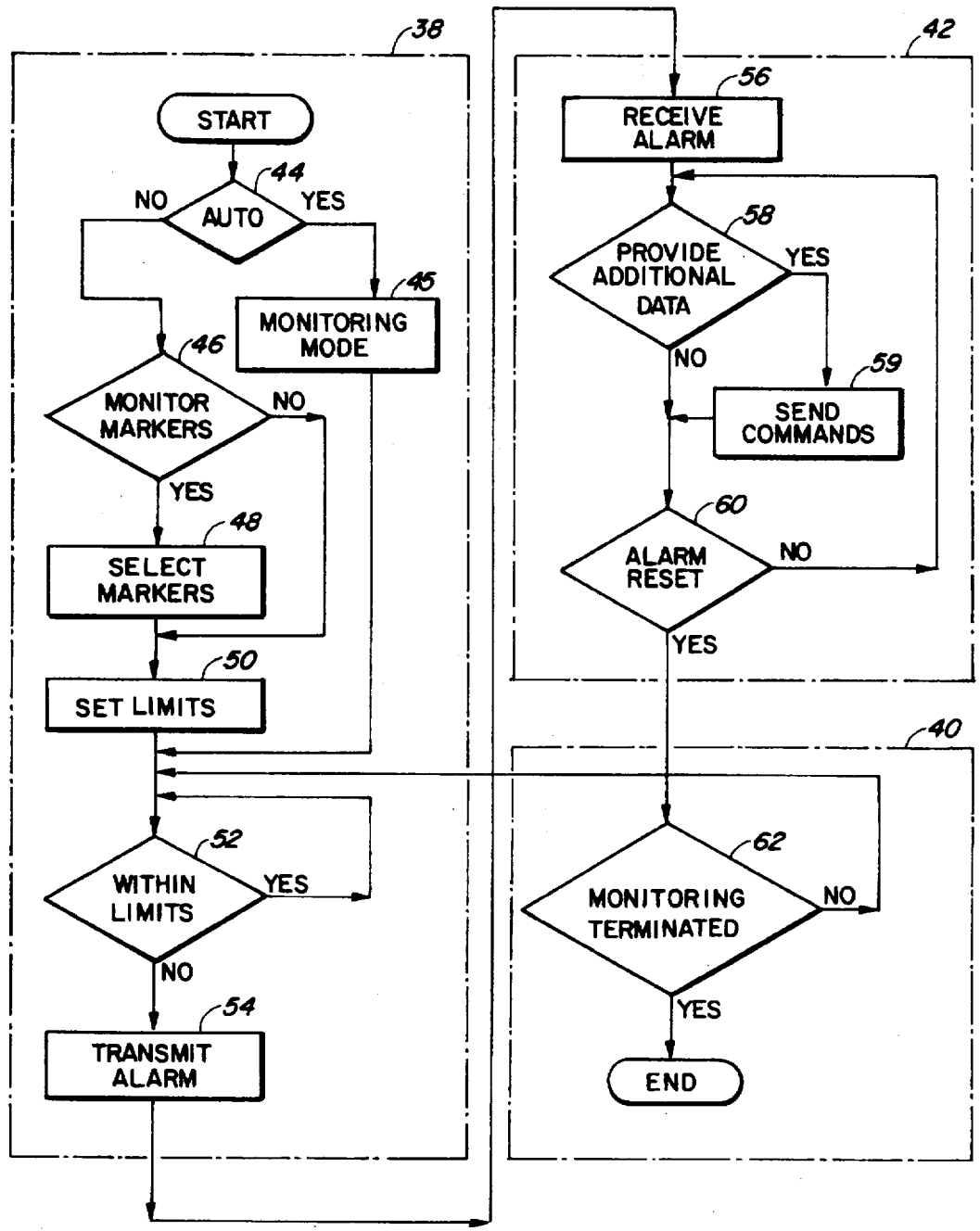
FIG. 4 is a logic flow diagram of the control programs that are used to direct the operation of the monitoring system in accordance with the present invention.

Computer programs used to control the monitoring unit 10 and the central monitoring station 12 are diagrammed in FIG. 4. Blocks 38 and 40 represent features of a preferred embodiment of the monitoring unit control program and block 42 represent steps performed by a preferred embodiment of the central monitoring station program. A physician or medical staff member typically selects various operating parameters for the monitoring unit 10 in blocks 38 and 40. The central monitoring station program steps contained within block 42 are generally under the control of a medical staff member at the central monitoring station 12. After placing the telemetry head 14 (FIG. 1) near to the implantable medical device 16 (FIG. 1) and initiating the monitoring unit program, the system decides at a test 44 based on a physician input whether or not to invoke an automatic monitoring routine. If the implantable medical device 16 (FIG. 1) is a cardiac stimulating device, the implantable medical device 16 (FIG. 1) will generally be capable of transmitting either physiological data, such as a patient's digitized intracardiac electrogram, or event markers which represent various cardiac and pacemaker events that have been detected and identified by the implantable medical device 16 (FIG. 1). For example, when R-waves are detected, digital signals representing the letter "R" can be transmitted to the monitoring unit 10 (FIG. 1) via telemetry. If automatic monitoring is invoked at the test 44, the monitoring unit 10 (FIG. 1) enters a predetermined monitoring mode 45, in which, for example, the monitoring unit 10 (FIG. 1) calculates the patient's heart rate by measuring the time elapsed between R-waves. With automatic monitoring, permissible upper and lower limits of the R-wave interval are set by the monitoring unit control program according to default limits.

If it is decided at the test 44 to manually set up the monitoring unit 10 (FIG. 1), then the system determines at a test 46, based on physician input, whether the monitoring unit 10 (FIG. 1) should monitor event markers. If event markers are to be monitored, the system selects which specific markers are to be monitored at a step 48, with physician input. At a step 50 limits are selected, such as the minimum and maximum heart rate permitted before an alarm is triggered.

The monitoring unit control program loops continuously at a test 52, until an alarm condition is determined to exist. As shown in FIG. 1, the implantable medical device 16 interacts with the monitoring unit 10 via telemetry. Depending on the capabilities of the implantable medical device 16, data and markers may be telemetered to the monitoring unit 10 either periodically or continuously. If desired, the implantable medical device 16 can be directed to transmit information to the monitoring unit 10, regardless of whether any confirming signals are received from the monitoring unit 10. Alternatively, the transmission protocol can involve handshaking. If necessary, the monitoring unit 10 can transmit a request for each item of data or marker that is sent from the implantable medical device 16. Preferably, however, the implantable medical device 16 can be directed to transmit data and markers to the monitoring unit 10 with a single command.

At the test 52 (FIG. 4) the monitoring unit control program may analyze the physiological data to determine whether the alarm condition exists. For example, if the monitoring unit 10 is provided with a patient's intracardiac electrogram, the monitoring unit 10 can analyze the intracardiac electrogram to determine whether a patient's heart is beating. If the intracardiac electrogram signal is weaker than it should be, or if it drops suddenly, an alarm condition exists. If desired, the monitoring unit 10 can be instructed to determine that an alarm condition exists when multiple conditions indicate that the patient's condition warrants an alarm. For example, the monitoring unit can be instructed to generate an alarm signal when a patient's heart rate is abnormally slow and the patient's heart rate changes suddenly.

Although the monitoring unit 10 can be set to monitor only the raw physiological data transmitted by the implantable medical device 16, if event markers are transmitted, the monitoring unit 10 can monitor the patient's condition more accurately and in greater detail. For example, if the implantable medical device 16 is a cardiac stimulating device, the time between received R-wave markers may be used as to calculate the patient's heart rate. The monitoring unit 10 can also analyze additional markers, such as those that identify P-waves and ventricular pacing pulses, to monitor the patient's condition. If desired, the monitoring unit control program can emulate the main operating program of the implantable medical device 16. As the monitoring unit 10 receives marker information from the implantable medical device 16 it can be determined whether the implantable medical device 16 has detected a significant physical condition in the patient.

One advantage of analyzing marker information is that this approach allows the monitoring unit 10 to avoid generating unwarranted alarm signals. For example, if the implantable medical device 16 is a cardiac stimulating device, the operation of the implantable medical device 16 may occasionally involve dropping a pacing pulse to terminate an episode of pacemaker mediated tachycardia ("PMT"). A PMT episode may occur when a pulse that is applied to a patient's ventricle is fed back to the patient's atrium via a retrograde conduction path in the heart. If the cardiac stimulating device (implantable medical device 16) is tracking the patient's atrial heart rate, the pulse that is fed back may be mistaken for the patient's normal sinus rhythm, which results in the application of increasingly fast pacing pulses to the patient's ventricle, until the maximum allowed pacing rate is reached. Although the maximum pacing rate may be less than the alarm signal threshold, it is generally desirable to attempt to terminate a PMT episode by dropping a pacing pulse after a set number of pulses have been applied at the maximum rate. However, unless the dropped pulse is accounted for by the monitoring unit 10, it may appear that the patient's heart rate is too slow, which could result in the generation of an alarm signal. The monitoring unit control program therefore may emulate the main operating program of the implantable medical device 16, so that if a pulse is dropped to terminate a PMT episode an erroneous alarm signal will not be generated by the monitoring unit 10.

Another advantage of analyzing marker information is that subtle aspects of the patient's condition can be inferred from the markers which would not be readily ascertainable using conventional monitoring equipment. For example, the monitoring unit 10 (FIG. 1) can take into account the existence of pacemaker mediated tachycardiac, effects due to changes in the sensing and capture thresholds of the cardiac stimulating device, and the results of abnormal sensor responses.

Returning to FIG. 4, if the monitoring unit 10 (FIG. 1) determines that an alarm condition exists, which indicates that a patient's condition requires attention, the bus interface 24 (FIG. 1) is used to transmit an alarm signal at a step 54 to the central monitoring station 12 (FIG. 1), which receives the alarm signal at a step 56. At a test 58, the system decides, based on input from a member of the staff at the central monitoring station 12 (FIG. 1), whether to notify the appropriate medical personnel, or whether to monitor the patient's condition in more detail at the central monitoring station 12 (FIG. 1). For example, the staff member can direct the system to send commands at a step 59 to the monitoring unit 10 (FIG. 1) via the bus 26 (FIG. 1) to direct the monitoring unit 10 (FIG. 1) to transmit the patient's intracardiac electrogram to the central monitoring station 12 (FIG. 1), where it can be examined in detail by the staff before additional medical personnel are notified. Real-time physiological data is selectively available, because it may not be feasible to simultaneously transmit intracardiac electrogram data from all the monitoring units in use due to the limited bandwidth of the bus 26. Preferably, members of the medical staff can direct the monitoring unit 10 to transmit patient data to the central monitoring station at any time, not only after an alarm condition has been determined to exist.

At a test 60, the central monitoring station control program will loop continuously until the central monitoring station 12 (FIG. 1) receives signals from the monitoring unit 10 (FIG. 1) indicating that the alarm has been responded to and reset. As shown at test 62, if medical personnel respond to the alarm and no additional monitoring is desired, the monitoring unit control program terminates. If further monitoring is desired, the monitoring unit control program returns to test 52.

Although the monitoring unit 10 (FIG. 1) may be implemented using a tablet computer 30 and base station 32, as shown in FIG. 2, or a flat panel touch screen approach as shown in FIG. 3, it will be appreciated that other computer-based alternatives are also feasible, such as implementing the monitoring unit control program on a tablet computer 30 that does not have a base station 32 or using a conventional personal computer which has an appropriate bus interface card and a telemetry port. Arrangements are also possible that are not computer-based, such as using dedicated control circuitry to implement the monitoring unit 10 shown in FIG. 1. Further, it is possible to use a bus interface 24 that can transmit data signals via the bus 26, but cannot receive commands from the central monitoring station 12. It is also possible to eliminate the bus interface and only use the monitoring unit 10 as a stand-alone unit. Such an arrangement might be desirable in a low-cost monitoring unit 10.

Figure 5:
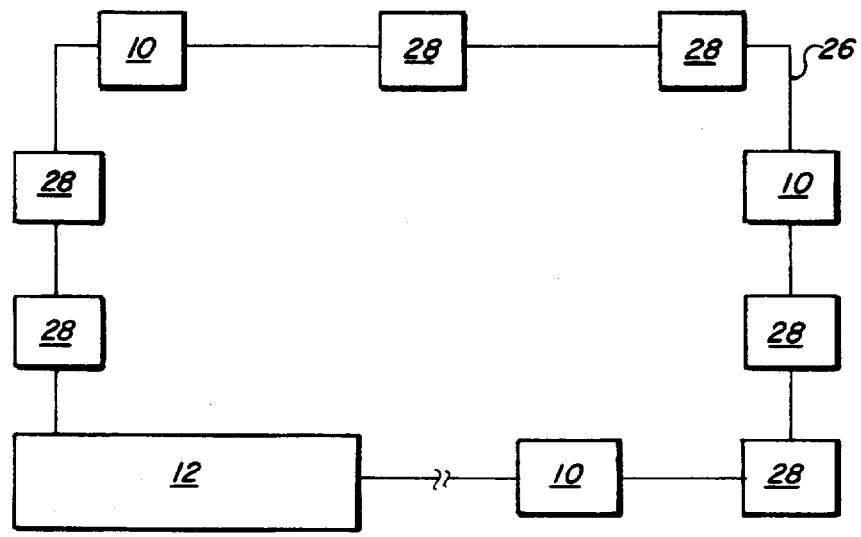
FIG. 5 is a schematic block diagram of the monitoring system in a ring configuration in accordance with the present invention.

The bus 26 can be a simple set of twisted-pair wires, a shielded multiple conductor bus, coaxial cable, or optical fiber. If desired, the monitoring unit 10 can communicate with the central monitoring station 12 using free space as the bus medium, for example, by using a radio or optical link. A preferred embodiment of the monitoring system 8 uses a bus architecture, however, it is also possible to use other topologies such as a ring or star, as shown in FIGS. 4 and 5, respectively. If a ring or star configuration is used, the bus interface 24 (FIG. 1) may use standard ring or star communication protocols for interfacing with the bus 26.

Thus a monitoring system is provided that monitors the condition of a patient by analyzing physiological data received from implantable medical devices. The monitoring system has at least one monitoring unit that may be connected to a central monitoring station. If the monitoring unit determines that a patient's physiological condition warrants attention, the monitoring unit generates an alarm signal, which may be an audible alarm, a visual alarm, or an alarm signal that is transmitted to the central monitoring station.

One skilled in the art will appreciate that the present invention can be practiced by other than the described embodiments, which are presented for the purposes of illustration and not of limitation, and the present invention is limited only by the claims that follow.

What is claimed is:

1. A monitoring system for monitoring the physiological condition of a patient who has an implantable cardiac stimulating device capable of transmitting data that is representative of the physiological condition of the patient and data that is representative of the condition of the device, the monitoring system comprising:

at least one monitoring unit that may operate unattended, the monitoring unit having:
      a telemetry head for receiving the data that is transmitted from the implantable cardiac stimulating device,
      a control unit for receiving the data from the telemetry head, the control unit comprising analyzing means for analyzing the received data to determine whether the implantable cardiac stimulating device is operating properly; status of the physiological condition of the patient and whether an alarm condition exists,
      an input interface for permitting programming of the control unit, and
      transmission means connected to the control unit for transmitting data and analyses and for transmitting an alarm signal if the control unit determines that an alarm condition exists; and
   a central monitoring station, remote from the patient, for receiving the alarm signal, data and analyses when transmitted from the monitoring unit by the transmission means and wherein the central monitoring station comprises means for displaying that an alarm condition exists.

2. The monitoring system of claim 1, further comprising:
   a bus connecting the monitoring unit to the central station, and wherein the transmission means connected to the control unit comprises a bus interface connected to the bus.

3. The monitoring system of claim 2, wherein the monitoring unit comprises:
   a tablet computer to which the telemetry head is coupled; and
   a base station, to which the tablet computer can be coupled, and which contains the bus interface.

4. The monitoring system of claim 1, wherein the control unit comprises:
   means for receiving physiological data transmitted by the implantable cardiac stimulating device;
   a monitoring unit control program; and
      means for executing the monitoring unit control program, whereby the monitoring unit control program determines whether the alarm condition exists based on an analysis of the physiological data.

5. The monitoring system of claim 1, wherein the monitoring unit comprises means for continually receiving data from the implantable cardiac stimulating device.

6. The monitoring system of claim 1, wherein the central monitoring station comprises means for periodically generating alarm signal requests.

7. The monitoring system of claim 1, wherein the monitoring unit comprises means for transmitting the alarm signal asynchronously and wherein the central monitoring station comprises means for receiving the alarm signal from the monitoring unit asynchronously.

8. A system for monitoring a person's physical condition, comprising:

an implantable cardiac stimulating device capable of transmitting event markers and physiological data;

at least one monitoring unit that may operate unattended, the monitoring unit having:

a telemetry head for receiving the event markers and physiological data transmitted by the implantable cardiac stimulating device, a control unit for receiving and analyzing the event markers and physiological data from the telemetry head, said control unit comprising analyzing means for analyzing the event markers and physiological data and alarm determination means for determining whether an alarm condition exists, and transmission means connected to the control unit for transmitting event markers, analyses and for transmitting an alarm signal if the control unit determines that an alarm condition exists; and a central monitoring station for receiving the alarm signal, event markers, physiological data and analyses when transmitted from the monitoring unit by the transmission means.

9. The system of claim 8, wherein the monitoring unit further comprises:

an input interface for programming the control unit.

10. The system of claim 9, wherein the monitoring unit comprises:

a tablet computer to which the telemetry head is coupled; and a base station, to which the tablet computer can be coupled, and which contains the bus interface.

11. The system of claim 8, further comprising:

a bus connecting the monitoring unit to the central station, and wherein the transmission means connected to the control unit comprises a bus interface connected to the bus.

12. The system of claim 8, wherein the analyzing means of the control unit comprises means for determining the physiological condition of the person's heart.

13. The system of claim 8, wherein the analyzing means of the control unit comprises means for determining the condition of the implantable cardiac stimulating device.

14. The system of claim 8, wherein the monitoring unit comprises means for continually receiving event markers and physiological data transmitted from the implantable cardiac stimulating device.

15. The system of claim 8, wherein the central monitoring station comprises means for periodically generating alarm signal requests.

16. The system of claim 8, wherein the monitoring unit comprises means for transmitting the alarm signal asynchronously and wherein the monitoring unit comprises means for transmitting the alarm signal asynchronously.

17. The system of claim 8, wherein the monitoring unit comprises means for unattended operation.

18. The system of claim 17, wherein the monitoring unit comprises means for producing an alarm signal.

19. The system of claim 18, wherein the analyzing means of the control unit comprises means for performing a plurality of analyses on a plurality of event markers and physiological data representing a plurality of device and physiological conditions and wherein the alarm determination means comprises means for determining an alarm condition based upon the plurality of analyses.

20. A method for unattended monitoring of the physiological condition of a patient who has an implanted cardiac stimulating device and for the unattended monitoring of the device itself, the method comprising the steps of:

transmitting event markers and physiological data from the implanted cardiac stimulating device;

receiving the transmitted event markers and physiological data with a monitoring unit;

analyzing the event markers and physiological data with a control unit associated with the monitoring unit to determine if an alarm condition exists; and transmitting an alarm signal to a central monitoring station when it is determined that an alarm condition exists.

21. The method of claim 20 wherein the step of receiving the event markers and physiological data transmitted form the implantable cardiac stimulator comprises receiving the event markers and physiological data continually.

22. The method of claim 20 further comprises the step of generating alarm signal requests at the central monitoring station.

23. The method of claim 20 wherein the step of transmitting the alarm signal to the central monitoring station asynchronously.

24. The method of claim 20 wherein the step of transmitting the alarm signal to the central monitoring station comprises the steps of:

generating buffered data output signals with a bus interface contained within the monitoring unit; and providing the buffered data output signals to a bus that is coupled between the bus interface and the central monitoring station.

25. The method of claim 20, wherein analyzing the event markers and physiological data further comprises the step of:

determining if a plurality of parameters exceed their respective predetermined acceptable limits in order to determine if an alarm condition exists.

* * * * *